US00PP24746P2

(12) United States Plant Patent
van Vliet

(10) Patent No.: US PP24,746 P2
(45) Date of Patent: Aug. 12, 2014

(54) ***THUJA* PLANT NAMED 'GOLDEN BRABANT'**

(50) Latin Name: *Thuja occidentalis*
Varietal Denomination: Golden Brabant

(75) Inventor: Sander van Vliet, Stroe (NL)

(73) Assignee: Van Vliet Newplants B.V., Stroe (NL)

( * ) Notice: Subject to any disclaimer, the term of this patent is extended or adjusted under 35 U.S.C. 154(b) by 169 days.

(21) Appl. No.: 13/507,129

(22) Filed: Jun. 6, 2012

(51) Int. Cl.
*A01H 7/00* (2006.01)

(52) U.S. Cl.
USPC ..... Plt./213

(58) Field of Classification Search
USPC ..... Plt./213
See application file for complete search history.

(56) References Cited

U.S. PATENT DOCUMENTS

PP24,012 P2 * 11/2013 Hoof ..... Plt./213

* cited by examiner

*Primary Examiner* — June Hwu
*Assistant Examiner* — Keith Robinson
(74) *Attorney, Agent, or Firm* — Penny J. Aguirre

(57) ABSTRACT

A new cultivar of *Thuja occidentalis* named 'Golden Brabant' that is characterized by its compact narrowly ovate to slightly columnar plant habit, its yellow-green foliage, and its dense branching.

2 Drawing Sheets

Botanical classification: *Thuja occidentalis.*
Varietal denomination: 'Golden Brabant'.

BACKGROUND OF THE INVENTION

The present invention relates to a new and distinct cultivar of *Thuja occidentalis* and will be referred to hereafter by its cultivar name, 'Golden Brabant'. 'Golden Brabant' represents a new cultivar of northern white cedar, an evergreen tree grown for landscape use.

The inventor discovered this new *Thuja* (un-patented) as a naturally occurring branch mutation of 'Brabant' (not patented) that was growing in a container at his nursery in summer of 2004 in Stroe, The Netherlands.

Asexual propagation of the new cultivar was first accomplished by softwood cuttings in Stroe, The Netherlands in October 2004 by the Inventor. Further asexual propagation by softwood cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Golden Brabant' as a unique cultivar of *Thuja occidentalis.*

1. 'Golden Brabant' exhibits yellow-green foliage.
2. 'Golden Brabant' is densely branched.
3. 'Golden Brabant' exhibits a compact narrowly ovate to slightly columnar plant habit.

The parent plant of 'Golden Brabant', 'Brabant', differs from 'Golden Brabant' in having a more open plant habit, less dense branching, and foliage that is more yellow in color. 'Golden Brabant' can be most closely compared to the cultivars 'Yellow Ribbon' (not patented), 'Thusid1' (U.S. Plant Pat. No. 22,003), and 'Golden Anne' (U.S. Plant Pat. No. 24,012) 'Yellow Ribbon' differs from 'Golden Brabant' in having a relatively loose habit, being moderately branched and in having foliage more yellow in color. 'Thusid1' differs from 'Golden Brabant' in having yellow foliage only on the new growing tips, in having a more columnar plant habit, and in having finer textured foliage. 'Golden Anne' differs from 'Golden Brabant' in having a broader plant habit; ovate to conical, rather than narrowly ovate to slightly columnar.

BRIEF DESCRIPTION OF THE DRAWING

The plant and plant parts depicted in the accompanied photographs illustrate the characteristics of 'Golden Brabant'. The photographs were taken of six year-old plants grown outdoors in 30-liter containers in Stroe, The Netherlands.

DETAILED BOTANICAL DESCRIPTION

Figure 1:
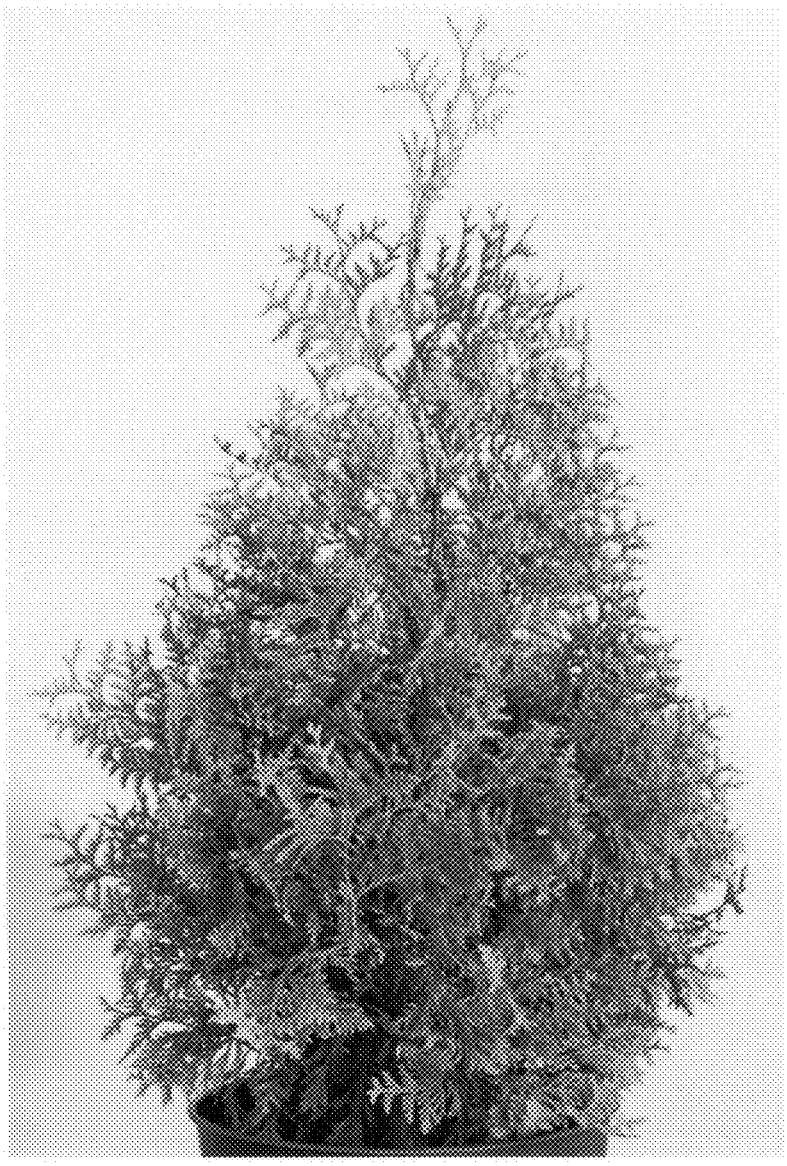
FIG. 1 provides an overall view of the habit and dense branching of 'Golden Brabant'.
Figure 2:
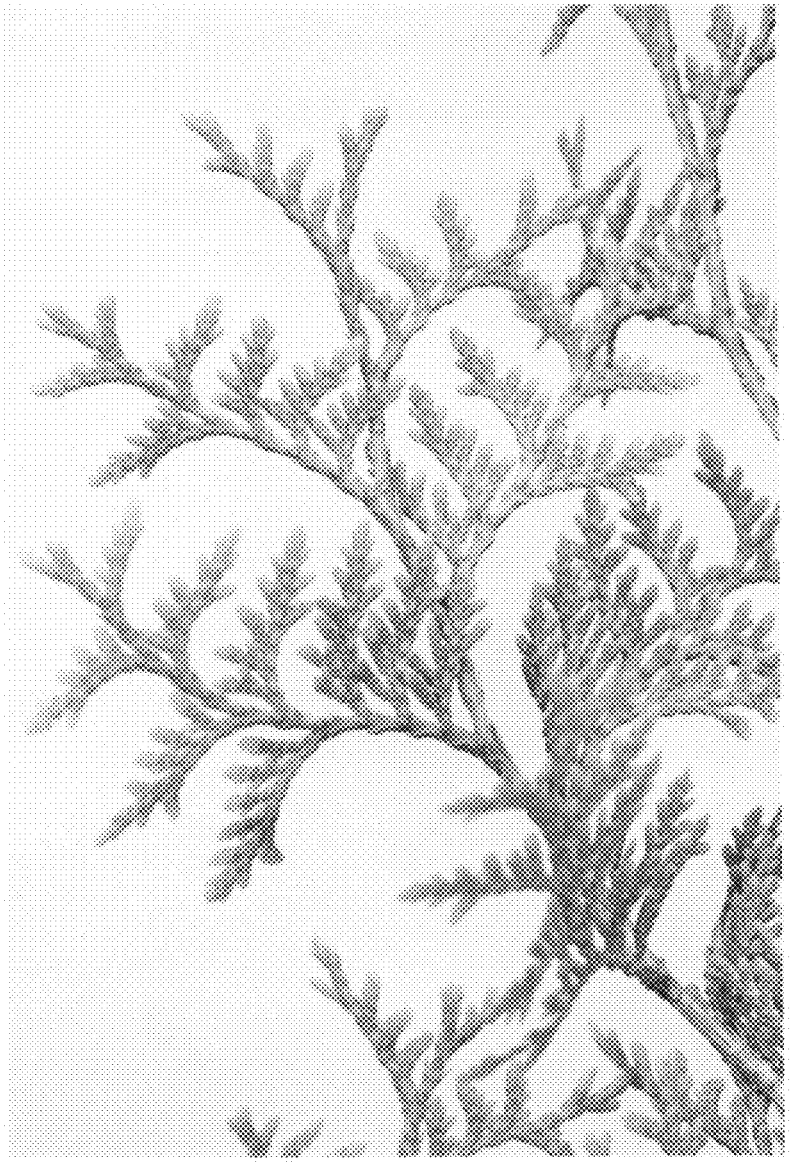
FIG. 2 provides a close-up view of the foliage of 'Golden Brabant'. The colors in the photographs are as close as possible with the photographic and printing technology utilized. The color values cited in the detailed botanical description accurately describe the colors of the new *Thuja.*

The following is a detailed description of the new cultivar as taken from six year-old plants as grown outdoors in 30-liter containers in Stroe, The Netherlands with average day temperatures ranging from 10° to 20° C. and average night temperatures ranging from 1° to 12° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type*.—Coniferous, evergreen, tree for landscape use.

*Growth habit*.—Broad upright, compact, narrowly ovate to slightly columnar with dense branching.

*Height and spread*.—An average of 81.5 cm in height and 49 cm in width.

*Hardiness*.—At least in U.S.D.A. Zones 6 to 9.

*Diseases and pests*.—No unique susceptibility or resistance to pests and diseases has been observed.

*Environmental*.—High tolerance to wind and rain.

*Root description*.—Fibrous, moderately branched, moderately thick, about 174A in color.

*Growth rate*.—Moderate, grows an average of 15 cm per year as grown in The Netherlands.

*Propagation*.—Softwood cuttings.

Stem description:

*Main stems*.—Typically one, an average of 70 cm in length and 1 cm in diameter as measured 10 cm from the tree base, round in shape, bark N199B in color, glossy and smooth surface.

*Branch shape*.—Rounded.

*Branch size*.—Average of 25.6 cm in length and 3 mm in diameter.

*Branch surface*.—Moderately glossy and smooth and covered with scale-like leaves.

*Branching*.—Very freely branching, average of 42 branches per main stem, an average of 20 branchlets per branch, each with an average of 12 secondary branchlets.

*Branch and branchlet arrangement*.—Alternate.

*Branch strength*.—Strong.

*Internode length*.—Average of 1.3 cm.

*Branch and branchlet color*.—One year-old stems; N144A to N144B.

Foliage description:

*Leaf arrangement*.—Opposite.

*Leaf attachment*.—Sessile.

*Leaf shape*.—Linear, scale-like.

*Leaf division*.—Simple.

*Leaf base*.—Cuneate.

*Leaf apex*.—Caudate.

*Leaf venation*.—Not visible.

*Leaf margins*.—Entire.

*Leaf fragrance*.—When crushed, scale-like leaves produce a very strong pleasant smell typical fragrance of *Thuja occidentalis*.

*Leaf surface*.—Upper and lower surfaces; smooth, glossy.

*Leaf color*.—Immature upper and lower surfaces; 151C to 151D, mature upper and lower surfaces; 144A to 144B, older mature foliage becomes 143A to 143B.

*Leaf size*.—An average of 3.5 mm in length and 1.5 mm in width.

*Leaf quantity*.—Average of 10,000 scale-like leaves per lateral branch.

*Leaf glands*.—Average of 0.5 mm in diameter, orbicular in shape and 152D in color.

Cone description: Neither male nor female cones have been observed.

It is claimed:

1. A new and distinct cultivar of *Thuja* plant named 'Golden Brabant' as herein illustrated and described.

* * * * *